(12) United States Patent
Murata et al.

(10) Patent No.: US 6,642,394 B2
(45) Date of Patent: Nov. 4, 2003

(54) PROCESS FOR PRODUCING (METH) ACRYLIC ANHYDRIDE AND PROCESS FOR PRODUCING (METH)ACRYLIC ESTER

(75) Inventors: Naoshi Murata, Hiroshima (JP); Kimio Tamura, Hiroshima (JP); Yasukazu Yoshida, Osaka (JP); Motomu Ohkita, Tokyo (JP)

(73) Assignee: Mitsubishi Rayon Co., Ltd., Tokyo (JP)

(*) Notice: Subject to any disclaimer, the term of this patent is extended or adjusted under 35 U.S.C. 154(b) by 0 days.

(21) Appl. No.: 10/363,912

(22) PCT Filed: Sep. 10, 2001

(86) PCT No.: PCT/JP01/07824
§ 371 (c)(1),
(2), (4) Date: Mar. 10, 2003

(87) PCT Pub. No.: WO02/20454
PCT Pub. Date: Mar. 14, 2002

(65) Prior Publication Data
US 2003/0181763 A1 Sep. 25, 2003

(30) Foreign Application Priority Data

Sep. 8, 2000 (JP) .......................................... 2000-272647
Sep. 14, 2000 (JP) .......................................... 2000-279997

(51) Int. Cl.⁷ .................. C07D 309/30; C07D 305/12; C07C 69/52

(52) U.S. Cl. ........................ 549/292; 549/313; 549/328; 549/329; 560/205

(58) Field of Search ................................ 549/292, 313, 549/328, 329; 560/205

(56) References Cited

U.S. PATENT DOCUMENTS 4,830,789 A  5/1989  Hinenoya et al. ........... 660/546

FOREIGN PATENT DOCUMENTS

| EP | 196520 | 10/1986 |
|---|---|---|
| EP | 231689 | 8/1987 |
| JP | 11-228560 | 8/1999 |
| JP | 2000-119220 | 4/2000 |

*Primary Examiner*—Amelia Owens
(74) *Attorney, Agent, or Firm*—Oblon, Spivak, McClelland, Maier & Neustadt, P.C.

(57) ABSTRACT

(Meth)acrylic acid is reacted with a fatty acid anhydride and the resultant reaction mixture is neutralized and washed with an aqueous alkaline solution having a pH of 7.5 to 13.5. Thus, high-purity (meth)acrylic anhydride can be industrially advantageously produced while avoiding polymerization. This (meth)acrylic anhydride is reacted with a secondary or tertiary alcohol in the presence of a basic compound which in 25° C. water has an acidity (pKa) of 11 or lower. Thus, a high-purity (meth)acrylic ester can be produced in high yield.

19 Claims, No Drawings

PROCESS FOR PRODUCING (METH) ACRYLIC ANHYDRIDE AND PROCESS FOR PRODUCING (METH)ACRYLIC ESTER

TECHNICAL FIELD

This invention relates to a process for producing (meth)acrylic anhydride, in particular, to a process for producing (meth)acrylic anhydride as a raw material for (meth)acrylic ester monomer which is usable as a raw material for polymer for semiconductor resist use. This invention also relates to a process for producing (meth)acrylic ester, in particular, to a process for producing (meth)acrylic ester as a raw material for polymer for semiconductor resist use.

BACKGROUND ART

As a process for producing (meth)acrylic anhydride, there have been known processes in which (meth)acrylic acid is reacted with (meth)acrylic chloride (Khim. Prom. (Moscow) (1969), 45 (11), 822–3) and in which (meth)acrylic acid is reacted with acetic anhydride and the resultant reaction product is distilled (Japanese Patent Laid-Open No. 62-158237).

The process in which (meth)acrylic anhydride is produced by reacting (meth)acrylic acid with (meth)acrylic chloride, however, involves generating an acidic gas, and therefore, requires a reactor made up of special materials which have a resistance to corrosion. Thus it is not suitable for the production in industrial scale.

On the other hand, in the process in which (meth)acrylic anhydride is produced by reacting (meth)acrylic acid with acetic anhydride and distilling the resultant reaction product, the materials for the reactor is not a problem, but it is hard to purify the (meth)acrylic anhydride into a high-purity product. That is, the distillation, a common purifying process, has a problem that concentrated (meth)acrylic anhydride is very likely to polymerize because it is exposed to high temperatures under an acidic condition in the final stage of distilling step in which (meth)acrylic acid, mixed acid anhydride of (meth)acrylic acid and acetic acid, and unreacted acetic anhydride are distilled off from an intended product.

A process is known in which (meth)acrylic esters are produced from (meth)acrylic anhydride and alcohols; however, this process is not suitable for industrially producing (meth)acrylic ester having the following the formula (3) or (4), which is useful in the electronic material applications, in particular, as a raw material monomer for polymer for semiconductor resist use, because it is hard to produce high-purity (meth)acrylic anhydride as a raw material for the esters, as described above. Specifically, there is a problem that the use of low-purity (meth)acrylic anhydride as a raw material causes a side reaction or a polymerization reaction, resulting in production of low-purity (meth)acrylic esters in low yield.

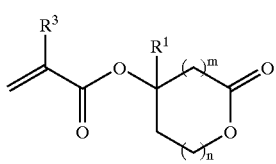

(3)

In the formula, $R^1$ represents hydrogen atom or alkyl group; n and m represent independently 0 or 1 as the number of methylene group; and $R^3$ represents hydrogen atom or methyl group.

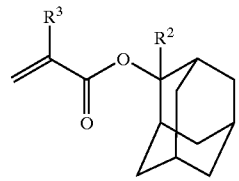

(4)

In the formula, $R^2$ represents alkyl group; and $R^3$ represents hydrogen atom or methyl group.

DISCLOSURE OF THE INVENTION

Accordingly, one object of this invention is to provide a process for industrially producing high-purity (meth)acrylic anhydride, especially (meth)acrylic anhydride used as a raw material for (meth)acrylic ester monomer which is usable as a raw material for polymer for semiconductor resist use, while avoiding polymerization. Another object of this invention is to provide a process for producing high-purity (meth)acrylic ester of a secondary or tertiary alcohol in high yield, in particular, a process for producing high-purity (meth)acrylic ester having the formula (3) or (4), which is a raw material monomer for polymer for semiconductor resist use, in high yield.

The inventors of this invention found that in the process of producing (meth)acrylic anhydride by reacting (meth)acrylic acid with a fatty acid anhydride, high-purity (meth)acrylic anhydride can be obtained by neutralizing the resultant reaction mixture with an aqueous alkaline solution while avoiding distillation, and accomplished this invention.

Specifically, this invention is a process for producing (meth)acrylic anhydride comprising a step of reacting (meth)acrylic acid with a fatty acid anhydride; and a step of neutralization-washing the resultant reaction mixture with an aqueous alkaline solution having a pH of 7.5 to 13.5.

In this process, preferably the above resultant reaction mixture is dissolved in a low-polar solvent prior to the above neutralization-washing step.

The (meth)acrylic anhydride produced in this process is suitable for the raw material for (meth)acrylic ester monomer, which is a raw material for polymer for semiconductor resist use.

Further, this invention is a process for producing (meth)acrylic ester which includes an esterifying step of reacting the (meth)acrylic anhydride produced by the above described process with a secondary or tertiary alcohol in the presence of a basic compound which in 25° C. water has an acidity (pKa) of 11 or less.

As the secondary or tertiary alcohol used in the reaction, are preferable alcohols having the following formula (1) or (2), and as the (meth)acrylic ester produced through the reaction, are preferable (meth)acrylic esters having the following formula (3) or (4).

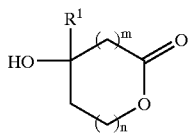

(1)

In the formula, $R^1$ represents a hydrogen atom or an alkyl group; and n and m represent independently 0 or 1 as the number of methylene group.

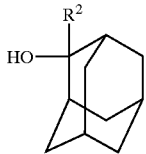

(2)

In the formula, $R^2$ represents alkyl group.

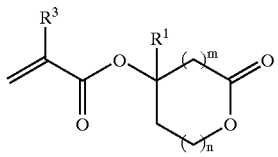

(3)

In the formula, $R^1$ represents a hydrogen atom or an alkyl group; n and m represent independently 0 or 1 as the number of methylene group; and $R^3$ represents a hydrogen atom or a methyl group.

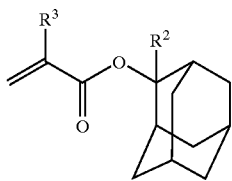

(4)

In the formula, $R^2$ represents an alkyl group; and $R^3$ represents a hydrogen atom or a methyl group.

When the (meth)acrylic ester thus produced is that expressed by the above formula (3), (meth)acrylic ester with higher-purity can be obtained by adding a washing step of washing the (meth)acrylic ester obtained after the above esterifying step with a low-polar solvent and then with an aqueous acid solution and/or an aqueous alkaline solution.

Further, when the (meth)acrylic ester thus produced is that expressed by the above formula (4), (meth)acrylic ester with higher-purity can be obtained by adding a washing step of washing the (meth)acrylic ester obtained after the above esterifying step with an aqueous alkaline solution and then with an aqueous acid solution. Further, thus obtained (meth)acrylic ester may be subjected to thin-film distillation to provide higher-purity (meth)acrylic ester.

The (meth)acrylic ester produced in accordance with the process of this invention is suitable for the raw material for polymer for semiconductor resist use.

BEST MODE FOR CARRYING OUT THE INVENTION

In this invention, (meth)acrylic anhydride is produced by reacting (meth)acrylic acid with a fatty acid anhydride. The term "(meth)acrylic acid", as is commonly used, means a general term for the acrylic acid and the methacrylic acid. Preferably the fatty acid anhydrides used in this invention are compounds having the following structural formula:

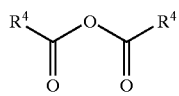

wherein $R^4$ represents alkyl group.

In the above formula, $R^4$ is preferably an alkyl group with 1 to 3 carbon atoms, and the two units of $R^4$ may be different, but preferably they may be generally the same.

The reaction temperature is preferably $-30°$ C. to $120°$ C., and more preferably $0°$ C. to $100°$ C. The higher the reaction temperature becomes, the higher the reaction rate becomes, and lower the reaction temperature becomes, the more the side reaction is inhibited. Preferably the reaction is conducted while removing the fatty acid produced as a by-product outside the system under reduced pressure. This reaction can be conducted without a solvent, but an inert solvent may be used depending on the situation. The inert solvents include, for example, n-hexane, toluene and xylene.

A catalyst may also be used for the reaction, if necessary, and the catalysts applicable include, for example, phosphoric acid, potassium acetate and sulfuric acid.

To inhibit polymerization during the reaction, preferably a polymerization inhibitor is appropriately used.

In this invention, the reaction mixture after the reaction step is neutralized with an aqueous alkaline solution havings a pH of 7.5 to 13.5. Preferably, the reaction mixture is dissolved in a low polar solvent prior to this neutralization step. When using a low polar solvent in the reaction, the solvent may remain as it is or may be removed after the reaction.

The low polar solvents applicable are those which can dissolve (meth)acrylic anhydride, are less soluble in water, and are easily distilled off from (meth)acrylic anhydride.

The low polar solvents as above include, for example, hydrocarbon solvents, and particularly preferable low polar solvents include, for example, aliphatic hydrocarbons such as n-hexane, n-heptane and n-pentane; and aromatic hydrocarbons such as toluene. The amount of the solvent used is usually 1 to 30 times the weight of (meth)acrylic anhydride, preferably 5 to 20 times the weight of the same. The larger amount of the low polar solvent leads to the higher effectiveness of the neutralization with an aqueous alkaline solution. The smaller amount of the low polar solvent leads to lowering the cost.

The lower pH value of the aqueous alkaline solution leads less decomposition of (meth)acrylic anhydride. The aqueous alkaline solutions applicable here are not particularly limited to specific ones, and they include, for example, aqueous solutions of hydroxides or carbonates of sodium or potassium. The neutralization-washing is performed at least once and appropriately repeated depending on the amount of the remaining impurities. Excess neutralization-washing leads to loss of (meth)acrylic anhydride, therefore, the neutralization-washing is stopped once the impurities reach the tolerable levels or less.

In an example of the processes of industrially operable neutralization-washing, steps include, by using a container equipped with a mechanism capable of removing the solution from its lower part, filling a solution into the container, adding an aqueous alkaline solution while stirring the mixture, stirring it adequately, allowing the mixture to stand still to occur layer-separation, and removing the water layer (the lower layer).

In the neutralization-washing step, preferably the reaction mixture is washed with water after the washing with an aqueous alkaline solution, depending on the situation.

This neutralization-washing step gives a mixed solution containing mainly (meth)acrylic anhydride and a low polar solvent. The (meth)acrylic anhydride is obtained after concentrating the mixed solution, for example, by distilling off the low polar solvent. At this point, acids such as (meth) acrylic acid have been already removed; therefore, even if the solution is heated, polymerization is hard to induce.

The (meth)acrylic anhydride produced in this manner is suitable for the raw material for (meth)acrylic ester monomer which is a raw material for polymer for semiconductor resist use, since it is low in impurities.

This invention is also a process for producing (meth) acrylic ester in which the (meth)acrylic anhydride produced in this manner is reacted with a secondary or tertiary alcohol in the presence of a basic compound which in 25° C. water has an acidity (pKa) of 11 or lower. This process is suitable for producing (meth)acrylic ester having the above formula (3) or (4) from a lactone alcohol having the above formula (1) or an adamantyl alcohol having the above formula (2), as secondary or tertiary alcohol.

In the lactone alcohols having the formula (1), $R^1$ represents hydrogen atom or alkyl group; when $R^1$ is alkyl group, though the number of the carbon atoms is not particularly limited, preferably $R^1$ is a hydrogen atom or an alkyl group with 1 to 5 carbon atoms from the viewpoint of reactivity, ease of purification and polymerizability. Particularly preferably $R^1$ is a hydrogen atom or a straight-chain alkyl group such as methyl group, ethyl group, n-propyl group and n-butyl group.

In the adamantyl alcohols having the above formula (2), $R^2$ is an alkyl group, though the number of the carbon atoms is not particularly limited, preferably $R^2$ is an alkyl group with 1 to 5 carbon atoms from the viewpoint of reactivity and polymerizability, particularly preferably $R^2$ is straight-chain alkyl group such as methyl group, ethyl group, n-propyl group and n-butyl group.

The acidity (pKa) in 25° C. water of the basic compound used as a catalyst in this ester synthesizing reaction is 11 or lower, and preferably 6 to 11. As the basic compound, are preferable amines and nitrogen-containing heterocyclic compounds whose nitrogen atoms may be members constituting a ring. Such basic compounds include, for example, triethylamine (pKa=10.72), pyridine (pKa=5.42), 2,6-dimethylpyridine (pKa=6.90), triethylenetetramine (pKa=3.25, 6.56, 9.08, 9.74), triethanolamine (pKa=7.76) and piperazine (pKa=5.59, 9.71).

Preferably the amount of the basic compound used is appropriately changed depending on the type of the secondary- or tertiary-alcohols used in the reaction. When the alcohol as a raw material is a lactone alcohol shown by the above formula (1), the amount is usually 0.1 to 3 mol, and preferably 0.5 to 2 mol per mol of the lactone alcohol shown by the above formula (1). And when the alcohol as a raw material is adamantyl alcohol shown by the above formula (2), the amount used is normally 0.1 to 3 mol, and preferably 0.5 to 2 mol per mol of the adamantyl alcohol shown by the above formula (2).

The lower limit of the reaction temperature in the ester synthesizing reaction is normally −20° C. or higher, preferably 10° C. or higher, and more preferably 40° C. or higher. And the upper limit of the reaction temperature is normally 120° C. or lower, preferably 100° C. or lower, and more preferably 80° C. or lower. The lower the reaction temperature is, the more the side reaction is inhibited.

The reaction time is not particularly limited; however, preferably the time is set to give the largest possible amount of intended product, taking into consideration the ratio of the (meth)acrylic ester produced as an intended product to the decomposition products of secondary or tertiary alcohols. The reaction time is normally 5 to 50 hours, and preferably 10 to 40 hours. The shorter the reaction time is, the more the side reaction is inhibited.

In the ester synthesis, inerts solvent, such as halogenated hydrocarbons, ethers, ketones and aromatic hydrocarbons, may be used, if necessary. In order to inhibit polymerization, preferably a polymerization inhibitor, such as hydroquinone and hydroquinone monomethyl ether, and oxygen are allowed to exist.

When the (meth)acrylic ester obtained in this manner is a highly polar monomer such as the (meth)acrylic ester represented by the formula (3), unreacted (meth)acrylic anhydride can be removed by dissolving the monomer in a polar solvent and washing the same with a low polar solvent as a poor solvent. The solvent used is not necessarily a special one, and the polar solvents applicable include, for example, a water-methanol mixed solvent, water, methanol and ethylene glycol. The low polar solvents applicable include, for example, aliphatic hydrocarbons such as n-hexane, n-heptane and n-pentane and aromatic hydrocarbons such as toluene. When using a water-methanol mixed solvent, methanol can be distilled off from the water-methanol mixed layer and (meth)acrylic ester shown by the formula (3) can be extracted with an appropriate solvent such as ethyl acetate.

There exist basic compounds, such as amine, used as a catalyst and an acid by-product such as (meth)acrylic acid in the extracted solution; therefore, the solution is washed with an aqueous acid solution and/or an aqueous alkaline solution. The aqueous acid solutions applicable include, for example, an aqueous solution of sulfuric acid and the aqueous alkaline solutions applicable include, for example, an aqueous solution of sodium hydroxide. If the pH values of these aqueous solutions are too high or too low, the (meth)acrylic ester shown by the formula (3) is liable to be decomposed; therefore, preferably their pH values fall in the weak-acid or weak-base range with a pH of 4 to 10. Lastly, the extract is appropriately washed with a neutral aqueous solution such as an aqueous solution of sodium chloride.

On the other hand, when the resultant (meth)acrylic ester is a low polar monomer such as (meth)acrylic ester represented by the formula (4), unreacted (meth)acrylic anhydride can be removed by dissolving the (meth)acrylic ester in a low polar solvent as a poor solvent and washing the same with an aqueous alkaline solution. The low polar solvent used is not necessarily a special one, and the low polar solvents applicable include, for example, aliphatic hydrocarbons such as n-hexane, n-heptane and n-pentane and aromatic hydrocarbons such as toluene. The types of the aqueous alkaline solutions used are not particularly limited, and they include, for example, an aqueous solution of sodium hydroxide and an aqueous solution of sodium hydrogencarbonate. There exists a basic catalyst, such as amine, in the (meth)acrylic ester having been washed with an aqueous alkaline solution, therefore, the solution is washed with an aqueous acid solution. The aqueous acid solutions used are not particularly limited, and they include, for example, an aqueous solution of sulfuric acid. If the pH value of the aqueous acid solution is too low, the (meth)acrylic ester shown by the formula (4) is liable to be decomposed; therefore, preferably its pH value falls in the weak-acid range with a pH of 4 or higher. Lastly, the solution is appropriately washed with a neutral aqueous solution such as an aqueous solution of sodium chloride.

If the (meth)acrylic ester shown by the formula (3) or (4) thus obtained is subjected to thin-film distillation, the metal impurities can be reduced to 50 ppb or less. The thin-film evaporator used here is not necessarily a special one, a commonly used one is applicable. Preferably this thin-film distillation is carried out at 100 to 200° C. under 1 to 1500 Pa.

The (meth)acrylic ester thus produced contains less impurities, and therefore, it is suitable for (meth)acrylic ester monomer used as a raw material for polymer for semiconductor use.

EXAMPLES

This invention will be described in details using examples, but this invention is not limited to them. The analyses in the examples were done by gas chromatography (hereinafter referred to as GC) and $^1$H-NMR.

The purity of each product was calculated from the peak area of GC according to the following equation.

Purity (%)=(A/B)×100

In the above equation, A represents the peak area of an intended product, (meth)acrylic anhydride or (meth)acrylic ester and B represents the sum of all the peak areas.

The isolation yield was calculated according to the following equation.

Isolation yield (%)=(C/D)×100

In the above equation, C represents the number of moles of an intended product (calculated by multiply the weight of a product by its purity and divide the product by the molecular weight of thee intended product) and D represents the number of moles of an alcohol or (meth)acrylic acid as a material.

Example 1

Synthesis of Methacrylic Anhydride

A glass flask equipped with a stirrer, a dropping funnel, a thermometer, a Liebig condenser and a receiver was charged with 8.61 g (0.1 mol) of methacrylic acid, 7.66 g (0.075 mol) of acetic anhydride, 0.037 g ($3.8 \times 10^{-4}$ mol) of phosphoric acid and 0.009 g of 4-hydroxy-2,2,6,6-tetramethyl-piperdine-N-oxyl (hereinafter referred to as HO-TEMPO), and the mixture was heated and stirred at 60° C. for 20 hours. After cooling the reaction mixture, 75 ml of n-hexane was added, and the mixture was washed with 75 ml of water twice, neutralized and washed with 75 ml of saturated aqueous solution of sodium hydrogencarbonate (pH=7.81) 5 times, washed with 75 ml of water once, and the hexane layer of the mixture was concentrated to obtain 1.67 g of methacrylic anhydride of 97% purity. The isolation yield of methacrylic anhydride was 21% on the basis of methacrylic acid as the material.

Synthesis of γ-Butyrolactone-3-ylmethacrylate

A glass flask equipped with a stirrer, two dropping funnels, a thermometer and a Dimroth condenser was charged with 6 g (52.5 mmol) of β-hydroxy-γ-butyrolactone, 12.9 g (78.8 mmol) of methacrylic anhydride of 97% purity which is obtained by the above process, 6.4 g (81.4 mmol) of pyridine, 40 g of 2-butanone and 0.02 g of HO-TEMPO, and the mixture was heated and stirred at 50° C. for 22 hours. 2-butanone was distilled off from the reaction mixture, 130 ml of methanol and 200 ml of water were added to the reaction mixture, and the mixture was washed with 130 ml of n-hexane twice. To the water layer where methanol has been evaporated, 160 ml of ethyl acetate and 4 g of sodium chloride were added to perform extraction. The organic layer was washed with 160 ml of 2% aqueous solution of sodium hydrogencarbonate twice, a 2% aqueous solution of sulfuric acid once and a 1% aqueous solution of sodium chloride once, and the ethyl acetate layer was concentrated to obtain 5.8 g of γ-butyrolactone-3-ylmethacrylate of 91% purity. The isolation yield of the resultant γ-butyrolactone-3-ylmethacrylate was 59% on the basis of β-hydroxy-γ-butyrolactone as a material. The $^1$H-NMR spectral datum of the resultant γ-butyrolactone-3-ylmethacrylate was as follows.

$^1$H-NMR (CDCl$_3$) 2.1 (3H, s), 2.8(1H, d, J=18.4 Hz), 3.0 (1H, dd, J=6.8 Hz, 18.4 Hz), 4,5 (1H, d, J=10.8 Hz), 4.7 (1H, dd, J=4.8 Hz, 10.8 Hz), 5.6 (1H, dd, J=4.8 Hz, 6.8 Hz), 5.8 (1H, s), 6.3 (1H, s).

Distillation of γ-Butyrolactone-3-ylmethacrylate 29 g of γ-butyrolactone-3-ylmethacrylate of 91% purity which was obtained by the above process was vacuum distilled at 134 to 140° C. under 27 to 200 Pa with a thin-film evaporator. In this operation, 1000 ppm of a compound was added as polymerization inhibitor which was formed by adding an average of 6 mol of ethylene oxide to 4-position of 4-hydroxy-2,2,6,6-tetramethyl-piperidine-N-oxyl. Amount of γ-butyrolactone-3-ylmethacrylate distilled was 25 g. The content of impurities in the distillate was 1.2% (the chlorine content was 0.68 ppm), the isolation yield was 51% (on the basis of β-hydroxy-γ-butyrolactone). The contents of Na, Mg, K, Ca, Mn, Fe and Cu, which were trace metal elements in the γ-butyrolactone-3-ylmethacrylate, were 50 ppb or less after the thin-film distillation, though they were 100 ppb or more before the distillation.

Example 2

Synthesis of 2-Methyl-2-adamantyl Methacrylate

A glass flask equipped with a stirrer, two dropping funnels, a thermometer and a Dimroth condenser was charged with 16.6 g (0.1 mol) of 2-methyl-2-adamantanol, 23.1 g (0.15 mol) of methacrylic anhydride of 97% purity which is obtained by the process of example 1, 15.7 g (0.155 mol) of triethylamine, 0.6 g (0.005 mol) of dimethylaminopyridine, 70 ml of toluene and 0.005 g of HO-TEMPO, and the mixture was heated and stirred at 50° C. for 31 hours. It was confirmed that 2-methyl-2-adamantyl methacrylate was formed in the reaction mixture in a yield of about 40%. The resultant 2-methyl-2-adamantyl methacrylate was chromatographed on silica gel to obtain 9.1 g of 2-methyl-2-adamantyl methacrylate.

The purity of the 2-methyl-2-adamantyl methacrylate thus far obtained was 99% and the isolation yield of the same was 39% (on the basis of 2-methyl-2-adamantanol).

The $^1$H-NMR spectral datum of the product was as follows.

$^1$H-NMR (CDCl$_3$) 1.6–2.4 (20H, m), 5.5 (1H, s), 6.1 (1H, s).

Example 3

Synthesis of Methacrylic Anhydride

A glass flask equipped with a stirrer, a dropping funnel, a thermometer, a Liebig condenser and a receiver was charged with 8.61 g (0.1 mol) of methacrylic acid, 7.66 g (0.075 mol) of acetic anhydride, 0.037 g ($3.8\times10^{-4}$ mol) of phosphoric acid and 0.009 g of HO-TEMPO, and the mixture was heated and stirred at 60° C. for 20 hours. After cooling the reaction mixture, 75 ml of n-hexane was added, and the mixture was washed with 75 ml of water twice, neutralization-washing was performed with 75 ml of aqueous solution of sodium hydroxide (pH=13.2) 3 times, washed with 75 ml of water once, and the hexane layer of the mixture was concentrated to obtain 2.45 g of methacrylic anhydride of 97% purity. The isolation yield of methacrylic anhydride was 31% on the basis of methacrylic acid as starting material.

Example 4

Synthesis of Polymer for Semiconductor Resist use

A flask equipped with a nitrogen-introducing opening, a stirrer, a condenser and a thermometer was charged with 20.0 parts of 1,4-dioxane under nitrogen atmosphere and the temperature of a water bath was increased to 80° C. while stirring the dioxane. A monomer solution was obtained by mixing 29.3 parts of 2-methacryloyloxy-2-methyladamanatane (abbreviated designation: MAdMA) obtained by the process of example 2, 21.2 parts of β-methacryloyloxy-γ-butyrolactone (abbreviated designation: HGBMA) obtained by the process of example 1, 62.5 parts of 1,4-dioxane and 1.9 parts of azobisisobutyronitrile. The monomer solution was added dropwise into the flask at a constant rate over 6 hours, and the temperature of the mixture was kept at 80° C. for 2 hours. Then, the resultant reaction mixture was diluted with tetrahydrfuran by 2 folds. Then, about 10-fold amount of methanol was added dropwise while stirring, to obtain a white precipitate (copolymer A-1). The precipitate thus obtained was filtrated and dried at 60° C. under reduced pressure for about 40 hours.

The weight average molecular weight of the obtained copolymer was 11,000 and the copolymer composition ratio was MAdMA/HGBMA=50/50% by mole.

A homogeneous solution was prepared by mixing 100 parts of the obtained copolymer, 2 parts of triphenylsulfoniumtriflate as a photo acid-generating agent, 0.1 parts of N-isopropylmethacrylamide and 500 parts of propyleneglycol monomethyl ether acetate as a solvent. This solution was filtrated through a membrane filter having 0.1 μm hole diameter to prepare a solution of resist composition. Then the resist composition solution was spin-coated on a silicon wafer, and pre-baked on a hot plate at 120° C. for 60 seconds to form a resist film 0.5 μm thickness. The resist film was then exposed to ArF eximer laser light with an eximer laser exposure equipment and subjected to post-exposure baking with a hot plate oven at 120° C. for 60 seconds. Then the film was developed with a 2.38% by weight aqueous solution of tetramethylammonium hydroxide at room temperature, washed with deionized water, and dried to form a resist pattern. The sensitivity and resolution of the resultant resistant pattern were 5.8 mJ/cm$^2$ and 0.13 μm, respectively, and the resist configuration was satisfactory.

Comparative Example 1

Synthesis of Methacrylic Anhydride

A glass flask equipped with a stirrer, a dropping funnel, a thermometer, a Liebig condenser and a receiver was charged with 8.61 g (0.1 mol) of methacrylic acid, 7.66 g (0.075 mol) of acetic anhydride, 0.037 g ($3.8\times10^{-4}$ mol) of phosphoric acid and 0.009 g of HO-TEMPO, and the mixture was heated and stirred at 60° C. for 20 hours. After cooling the reaction mixture, 75 ml of n-hexane was added, and the mixture was washed with 75 ml of water twice, neutralization-washing was performed with 75 ml of 20% aqueous solution of sodium hydroxide (pH=13.7), washed with 75 ml of water once, and the hexane layer of the mixture was concentrated to obtain 0.26 g of methacrylic anhydride of 97% purity. The isolation yield of methacrylic anhydride was 3.3% on the basis of methacrylic acid as the material.

Comparative Example 2

Synthesis of Methacrylic Anhydride

A glass flask equipped with a stirrer, a dropping funnel, a thermometer, a Liebig condenser and a receiver was charged with 138 g (1.6 mol) of methacrylic acid, 123 g (1.2 mol) of acetic anhydride, 0.78 g (0.008 mol) of phosphoric acid and 0.14 g of HO-TEMPO, and the mixture was vacuum heated at an internal temperature of 83 to 104° C. under 17.3 to 2.7 kPa. After distilling off the by-product of acetic acid and the starting material of methacrylic acid, attempts were made to obtain methacrylic anhydride by distillation; however, no methacrylic anhydride could be obtained because of the polymerization induced inside the flask.

Comparative Example 3

Synthesis of γ-Butyrolactone-3-ylmethacrylate

A glass flask equipped with a stirrer, two dropping funnels, a thermometer and a Dimroth condenser was charged with 245 g (2.4 mol) of 3-hydroxy-γ-butyrolactone and 1600 ml of methylene chloride under nitrogen stream, and one of the droping funnels was charged with 300 g (2.9 mol) of methacryloyl chloride and the other was charged with 313 g (3.1 mol) of triethylamine. After the nitrogen replacement, the inside of the flak was cooled to −60 to −70° C. in a dry ice—acetone bath. Triethyleamine and methacrylic chloride were added dropwise into the flask under stirring, in such a manner as to adjust the amount of triethyleamine to be in a little excess of that of methacrylic chloride. After completion of the dropping, stirring was continued for 3 hours. 820 ml of water was added to the reaction mixture, filtrated after adding a little amount of Celite, the filtrate was washed with 820 ml water three times using a separatory funnel, 200 g of magnesium sulfate was added to dry the reaction mixture, and the filtrate obtained by the filtration was concentrated to obtain 475 g of crude γ-butyrolactone-3-ylmethacrylate. The crude γ-butyrolactone-3-ylmethacrylate was vacuum distilled at 134 to 140° C. under 27 to 200 Pa with a thin-film evaporator. At that time, 1000 ppm of a compound was added as polymerization inhibitor which was formed by adding an average of 6 mol of ethylene oxide to 4-position of 4-hydroxy-2,2,6,6-tetramethyl-piperidine-N-oxyl. The distilled γ-butyrolactone-3-yl methacrylate was 209 g (1.19 mol). The content of impurities in the distillate was 3.0% (the chlorine content was 36 ppm), the isolation yield was 51% (on the basis of β-hydroxy-γ-butyrolactone). The $^1$H-NMR spectral datum of the product was as follows.

$^1$H-NMR (CDCl$_3$) 2.1 (3H, s), 2.8(1H, d, J=18.4 Hz), 3.0 (1H, dd, J=6.8 Hz, 18.4 Hz), 4,5 (1H, d, J=10.8 Hz), 4.7 (1H, dd, J=4.8 Hz, 10.8 Hz), 5.6 (1H, dd, J=4.8 Hz, 6.8 Hz), 5.8 (1H, s), 6.3 (1H, s).

The γ-butyrolactone-3-yl methacrylate obtained by this process contained 50 times as much chlorine as that of example 1, therefore, was inferior to the γ-butyrolactone-3-yl methacrylate of example 1 as a raw material for semiconductor resist use which is required to contain as little chlorine as possible.

Industrial Applicability

According to this invention, high-purity (meth)acrylic anhydride, in particular, high-purity (meth)acrylic anhydride as a raw material for (meth)acrylic ester monomer which is used as a raw material for polymer for semiconductor resist use can be industrially produced while avoiding polymerization.

Further, according to this invention, (meth)acrylic ester of secondary or tertiary alcohol, in particular, (meth)acrylic ester having the formula (3) and (4) which are raw material monomer for polymer for semiconductor resist use can be produced in a high yield and with high purity.

What is claimed is:

1. A process for producing (meth)acrylic anhydride, comprising:

a step of reacting (meth)acrylic acid with a fatty acid anhydride; and a step of neutralization-washing the resultant reaction mixture with an aqueous alkaline solution having a pH of 7.5 to 13.5.

2. The process for producing (meth)acrylic anhydride according to claim 1, wherein the resultant reaction mixture is dissolved in a low polar solvent prior to the neutralization-washing step.

3. The process for producing (meth)acrylic anhydride according to claim 1, wherein the (meth)acrylic anhydride produced is a raw material for (meth)acrylic ester monomer which is a raw material for polymer for semiconductor resist use.

4. A process for producing (meth)acrylic ester, comprising a esterifying step of reacting the (meth)acrylic anhydride produced by the process according to claim 1 with a secondary or tertiary alcohol in the presence of a basic compound which has an acidity (pKa) of 11 or less in 25° C. water.

5. The process for producing (meth)acrylic ester according to claim 4, characterized in that the secondary or tertiary alcohol is a compound having the following formula (1) or (2) and the (meth)acrylic ester produced has the formula (3) or (4):

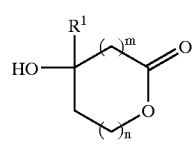

(1)

wherein $R^1$ represents hydrogen atom or alkyl group; and n and m represent independently 0 or 1 as the number of methylene group;

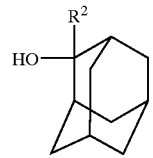

(2)

wherein $R^2$ represents alkyl group;

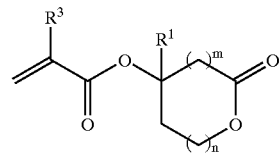

(3)

wherein $R^1$ represents hydrogen atom or alkyl group; n and m represent independently 0 or 1 as the number of methylene group; and $R^3$ represents hydrogen atom or methyl group;

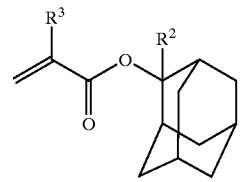

(4)

wherein $R^2$ represents alkyl group; and $R^3$ represents hydrogen atom or methyl group.

6. The process for producing (meth)acrylic ester according to claim 5, wherein the esterifying step is carried out at reaction temperatures of 80° C. or lower.

7. The process for producing (meth)acrylic ester according to claim 6, wherein the (meth)acrylic ester produced has the formula (3) and the process further comprises a washing step of washing the (meth)acrylic ester obtained after the esterifying step with a low polar solvent and further washing with an aqueous acid solution and/or an aqueous alkaline solution.

8. The process for producing (meth)acrylic ester according to claim 6, wherein the (meth)acrylic ester produced has the formula (4) and the process further comprises a washing step of washing the (meth)acrylic ester obtained after the esterifying step with an aqueous alkaline solution and further washing with an aqueous acid solution.

9. The process for producing (meth)acrylic ester according to claim 7, characterized in that the (meth)acrylic ester obtained after the washing step is subjected to thin-film distillation.

10. The process for producing (meth)acrylic ester according to claim 8, characterized in that the (meth)acrylic ester obtained after the washing step is subjected to thin-film distillation.

11. A process for producing (meth)acrylic ester, comprising a esterifying step of reacting the (meth)acrylic anhydride produced by the process according to claim 2 with a secondary or tertiary alcohol in the presence of a basic compound which has an acidity (pKa) of 11 or less in 25° C. water.

12. The process for producing (meth)acrylic ester according to claim 11, characterized in that the secondary or tertiary alcohol is a compound having the following formula (1) or (2) and the (meth)acrylic ester produced has the formula (3) or (4):

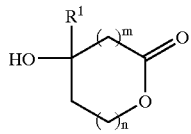
(1)

wherein $R^1$ represents hydrogen atom or alkyl group; and n and m represent independently 0 or 1 as the number of methylene group;

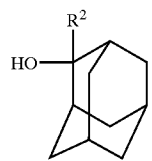
(2)

wherein $R^2$ represents alkyl group;

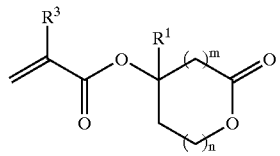
(3)

wherein $R^1$ represents hydrogen atom or alkyl group; n and m represent independently 0 or 1 as the n*umber of methylene group; and $R^3$ represents hydrogen atom or methyl group;

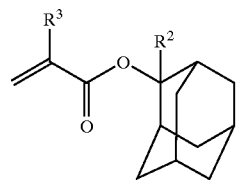
(4)

wherein $R^2$ represents alkyl group; and $R^3$ represents hydrogen atom or methyl group.

13. The process for producing (meth)acrylic ester according to claim 12, wherein the esterifying step is carried out at reaction temperatures of 80° C. or lower.

14. The process for producing (meth)acrylic ester according to claim 13, wherein the (meth)acrylic ester produced has the formula (3) and the process further comprises a washing step of washing the (meth)acrylic ester obtained after the esterifying step with a low polar solvent and further washing with an aqueous acid solution and/or an aqueous alkaline solution.

15. The process for producing (meth)acrylic ester according to claim 13, wherein the (meth)acrylic ester produced has the formula (4) and the process further comprises a washing step of washing the (meth)acrylic ester obtained after the esterifying step with an aqueous alkaline solution and further washing with an aqueous acid solution.

16. The process for producing (meth)acrylic ester according to claim 14, characterized in that the (meth)acrylic ester obtained after the washing step is subjected to thin-film distillation.

17. The process for producing (meth)acrylic ester according to claim 15, characterized in that the (meth)acrylic ester obtained after the washing step is subjected to thin-film distillation.

18. The process for producing (meth)acrylic ester according to claim 4, characterized in that the (meth)acrylic ester obtained after the washing step is subjected to thin-film distillation.

19. The process for producing (meth)acrylic ester according to claim 10, characterized in that the (meth)acrylic ester obtained after the washing step is subjected to thin-film distillation.

* * * * *